(12) United States Patent
Brenner

(10) Patent No.: US 10,786,214 B2
(45) Date of Patent: Sep. 29, 2020

(54) DENTAL X-RAY SENSOR HOLDER AND DENTAL X-RAY SENSOR SHEATH THEREFOR

(71) Applicant: DENTSPLY SIRONA Inc., York, PA (US)

(72) Inventor: Tod Brenner, Pequea, PA (US)

(73) Assignee: DENTSPLY SIRONA INC., York, PA (US)

( * ) Notice: Subject to any disclaimer, the term of this patent is extended or adjusted under 35 U.S.C. 154(b) by 47 days.

(21) Appl. No.: 15/658,760

(22) Filed: Jul. 25, 2017

(65) Prior Publication Data

US 2018/0028131 A1    Feb. 1, 2018

Related U.S. Application Data

(60) Provisional application No. 62/366,741, filed on Jul. 26, 2016, provisional application No. 62/401,956, filed on Sep. 30, 2016.

(51) Int. Cl.

| | |
|---|---|
| *A61B 6/14* | (2006.01) |
| *A61B 6/00* | (2006.01) |
| *G03B 42/04* | (2006.01) |
| *B29C 65/00* | (2006.01) |
| *G03B 42/06* | (2006.01) |

(52) U.S. Cl.
CPC ............... *A61B 6/145* (2013.01); *A61B 6/44* (2013.01); *A61B 6/4423* (2013.01); *G03B 42/042* (2013.01); *B29C 65/00* (2013.01); *G03B 42/06* (2013.01)

(58) Field of Classification Search
CPC .......... A61B 6/145; A61B 6/44; A61B 6/4423
See application file for complete search history.

(56) References Cited

U.S. PATENT DOCUMENTS

| | | | |
|---|---|---|---|
| 3,473,026 A | 10/1969 | Updegrave | |
| 5,090,047 A * | 2/1992 | Angotti | G03B 42/042 378/168 |
| 6,652,141 B1 | 11/2003 | Cianciosi | |
| 6,811,312 B2 | 11/2004 | Bratslavsky | |
| 7,004,627 B2 | 2/2006 | Strong | |
| 2002/0176539 A1 | 11/2002 | Da Rold | |
| 2002/0196903 A1 * | 12/2002 | Eppinger | A61B 6/14 378/168 |
| 2005/0259791 A1 | 11/2005 | Strong | |

(Continued)

FOREIGN PATENT DOCUMENTS

GB      1276165 A      6/1972

OTHER PUBLICATIONS

International Search Report; PCT/US2017/043634; Oct. 24, 2017 (completed); dated Nov. 2, 2017 (mailed).

(Continued)

*Primary Examiner* — Hugh Maupin
(74) *Attorney, Agent, or Firm* — Dentsply Sirona Inc.

(57) ABSTRACT

A dental x-ray sensor holder 1 and sheath 4 for affixing a sensor to a backing plate 2 of the holder 1. The dental x-ray sensor holder 1 and sheath 4 generally includes a sensor holder 1 with a backing plate 2, having one or more spring arms 3, and affixed to or formed contiguously with a proximal end of a bite block 9 of the holder 1. It also includes a sensor sheath adapted to secure a sensor to the backing plate for X-ray acquisition.

2 Claims, 16 Drawing Sheets

(56) References Cited

U.S. PATENT DOCUMENTS

| | | |
|---|---|---|
| 2005/0265522 A1 | 12/2005 | Manley |
| 2006/0018436 A1 | 1/2006 | Diederich |
| 2010/0027756 A1* | 2/2010 | Hof .................... G03B 42/042 |
| | | 378/170 |
| 2010/0177875 A1* | 7/2010 | Steward, Jr. ........... G03B 42/04 |
| | | 378/170 |
| 2010/0322386 A1 | 12/2010 | Steck |
| 2011/0299663 A1* | 12/2011 | Steward, Jr. ......... G03B 42/042 |
| | | 378/170 |
| 2015/0282772 A1* | 10/2015 | Winters ................ A61B 6/425 |
| | | 378/62 |

OTHER PUBLICATIONS

International Preliminary Report on Patentability; PCT/US2017/043634; Oct. 24, 2017 (completed); dated Nov. 2, 2017 (mailed).
Written Opinion of the International Searching Authority; PCT/US2017/043634; Oct. 24, 2017 (completed); dated Nov. 2, 2017 (mailed).

* cited by examiner

DENTAL X-RAY SENSOR HOLDER AND DENTAL X-RAY SENSOR SHEATH THEREFOR

BACKGROUND OF THE INVENTION

Field of the Invention

The present invention relates generally to a holder and a sheath and more specifically to a dental X-ray sensor holder and a corresponding dental X-ray sensor sheath for removably securing a sensor in said sheath to a backing plate of said holder for X-ray acquisition.

Related Art

A conventional dental X-ray acquisition can be performed by positioning an X-ray source on one side of a patient and transmitting X-rays through a site in the oral cavity to be irradiated, and toward an x-ray detector located in the oral cavity.

U.S. Pat. No. 3,473,026 discloses a device for positioning dental X-ray film within the mouth for producing radiographs. It is hereby incorporated by reference for background purposes.

In a manner similar to the use of x-ray films, holding and positioning devices have been developed for x-ray sensors and phosphor imaging plates.

One way Dental X-rays sensors have been positioned for image acquisition is through the use of adhesives. More specifically adhesives are used to bond a holder to an encapsulated film or sensor as disclosed in U.S. Pat. No. 6,811,312.

U.S. Pat. No. 7,004,627 discloses a barrier and cushioning apparatus for use with sensors as a means to avoid contamination of the sensor while providing reduced discomfort through the use of a cushion cover that may incorporate an integrated adhesive section for securing to a positioning accessory such as a sensor holder.

However these holders can be bulky and accompanying adhesives may be time consuming to apply to holders when multiple radiographs are needed. Moreover, some adhesives may not be suitable to be used in the oral cavity. It is therefore desired to create a holder that is compact, inexpensive, simple and eliminates the use of adhesives to hold X-ray detectors.

Multiple types of X-ray detectors exist. A dental X-ray film for example is positioned relative to the target site in a predetermined and secure manner in order to obtain a useful image.

More recently, traditional X-ray films have been replaced with X-ray sensors. An example of such a sensor is shown in U.S. Pat. No. 6,652,141 which is hereby incorporated by reference for background disclosure of X-ray sensors.

Phosphor imaging plates are also used in the dental industry. The imaging plate is irradiated and the x-ray shot is stored onto the imaging plate to be read later by a scanning machine or the like and the data is transferred to a storage or display device, such as a computer.

These and other type of devices that receive dental X-rays for dental purposes are hereinafter collectively referred to as dental X-ray imaging media, X-ray sensors, sensors, imagers, image media or the like. Any such devices that are sensitive to such X-rays is within the scope of the invention. It is envisioned that in the future, other type of dental imaging media will be developed using similar or perhaps completely different technologies. These all have at least some commonality in that they generally must fit within the oral cavity and they must be securely held in a desired location during the x-ray procedure.

It will be appreciated from the above discussion that the different image media holders while all accomplishing similar purposes, all operate in different manners. However, the need still exists to create a device that is compact, inexpensive, simple and eliminates the use of adhesives to hold X-ray detectors.

BRIEF SUMMARY OF THE INVENTION

Existing limitations associated with the foregoing, as well as other limitations can be overcome by a method and system for removably securing a sensor to a backing plate of a dental X-ray sensor holder using a sheath provided with a strap wherein the strap can receive the backing plate of the holder to physically impinge on it and thereby secure the sensor in position relative to the backing plate. The invention thus comprises a sensor holder with a backing plate, having one or more spring arms and affixed to or formed contiguously with a proximal end of a bite block of the holder, and a sensor sheath adapted to removably secure a sensor in said sheath to the backing plate of said holder for X-ray acquisition.

There has thus been outlined, rather broadly, some of the features of the invention in order that the detailed description thereof may be better understood, and in order that the present contribution to the art may be better appreciated. There are additional features of the invention that will be described hereinafter.

In this respect, before explaining at least one embodiment of the invention in detail, it is to be understood that the invention is not limited in its application to the details of construction or to the arrangements of the components set forth in the following description or illustrated in the drawings. The invention is capable of other embodiments and of being practiced and carried out in various ways. Also, it is to be understood that the phraseology and terminology employed herein are for the purpose of the description and should not be regarded as limiting.

An object is to provide a Dental X-ray sensor Holder and Sheath for operably affixing a sensor to a backing plate of said holder. The sheath also acts as a contamination barrier for the sensor.

Another object is to provide a Dental X-ray Sensor Holder and Sheath that eliminates the use of conventional adhesives to affix a sensor to a backing plate of a sensor holder.

Another object is to provide a Dental X-ray Sensor Holder and Sheath wherein the sheath is provided with a strap that is permanently affixed to the sheath to provide a means for attaching the sensor in the sheath to a backing plate of the sensor holder.

Another object is to provide a Dental X-ray Sensor Holder and Sheath wherein the backing plate of the holder, provided with spring arms, which when slid under the strap of the sheath causes the strap to pull on the sheath to tighten it around the sensor.

Another object is to provide a Dental X-ray Sensor Holder and Sheath that for use with different sizes of sensors by having a backing plate with spring arms wherein the arms can extend outwardly to tighten the sheath around the different sized sensors.

Another object is to provide a Dental X-ray Sensor Holder and Sheath wherein the holder is configured for anterior teeth X-ray acquisitions.

Another object is to provide a Dental X-ray Sensor Holder and Sheath wherein the holder is configured for posterior teeth X-ray acquisitions.

Another object is to provide a Dental X-ray Sensor Holder and Sheath wherein the holder is configured for bitewing horizontal X-ray acquisitions.

Another object is to provide a Dental X-ray Sensor Holder and Sheath wherein the holder is configured for bitewing vertical X-ray acquisitions.

Another object is to provide a Dental X-ray Sensor Holder and Sheath wherein the holder is configured for bitewing endodontic X-ray acquisitions.

Further features and advantages, as well as the structure and operation of various embodiments herein, are described in detail below with reference to the accompanying drawings.

To the accomplishment of the above and related objects, this invention may be embodied in the form illustrated in the accompanying drawings, attention being called to the fact, that the drawings are illustrative only, and that changes may be made in the specific construction illustrated and described within the scope of this application.

BRIEF DESCRIPTION OF THE DRAWINGS

The teachings claimed and/or described herein are further described in terms of exemplary embodiments. These exemplary embodiments are described in detail with reference to the drawings. These embodiments are non-limiting exemplary embodiments, in which like reference numerals represent similar structures throughout the several views of the drawings, and wherein:

DETAILED DESCRIPTION OF THE INVENTION

Figure 1:
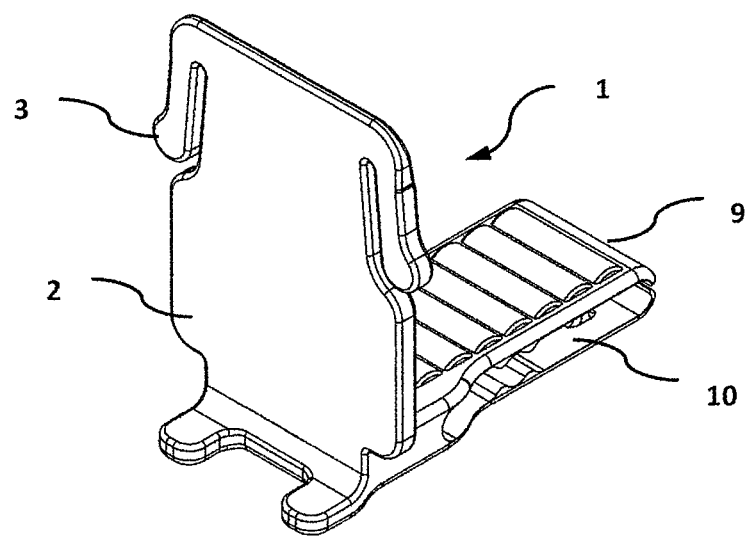
FIG. 1 is a perspective view of the preferred embodiment of the present invention, used for X-ray acquisitions of the anterior teeth.
Figure 2:
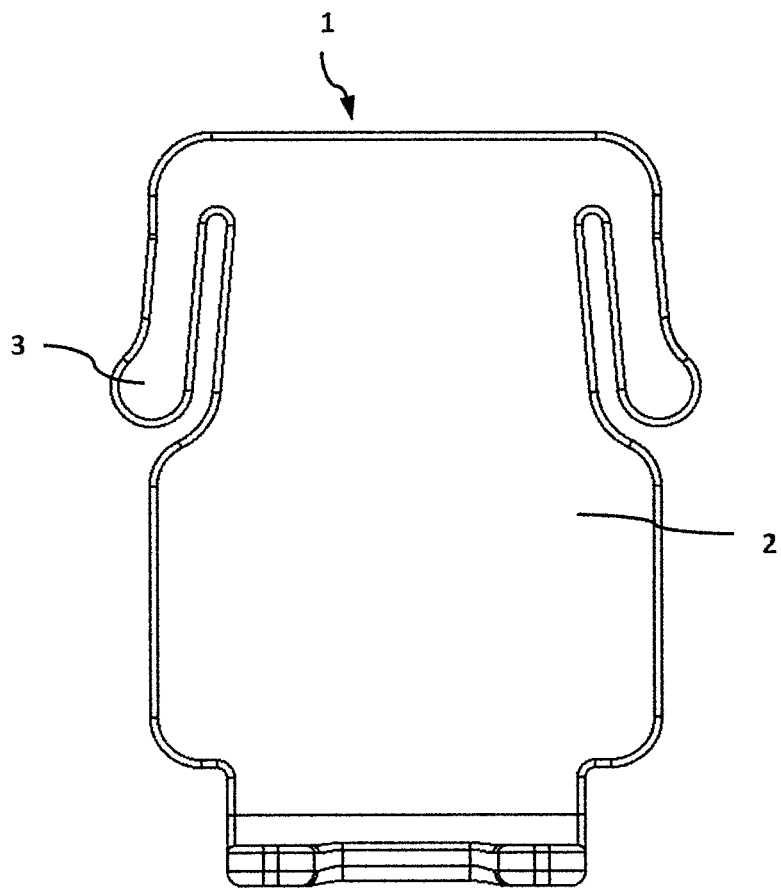
FIG. 2 illustrates a rear view of the sensor holder of FIG. 1.
Figure 3:
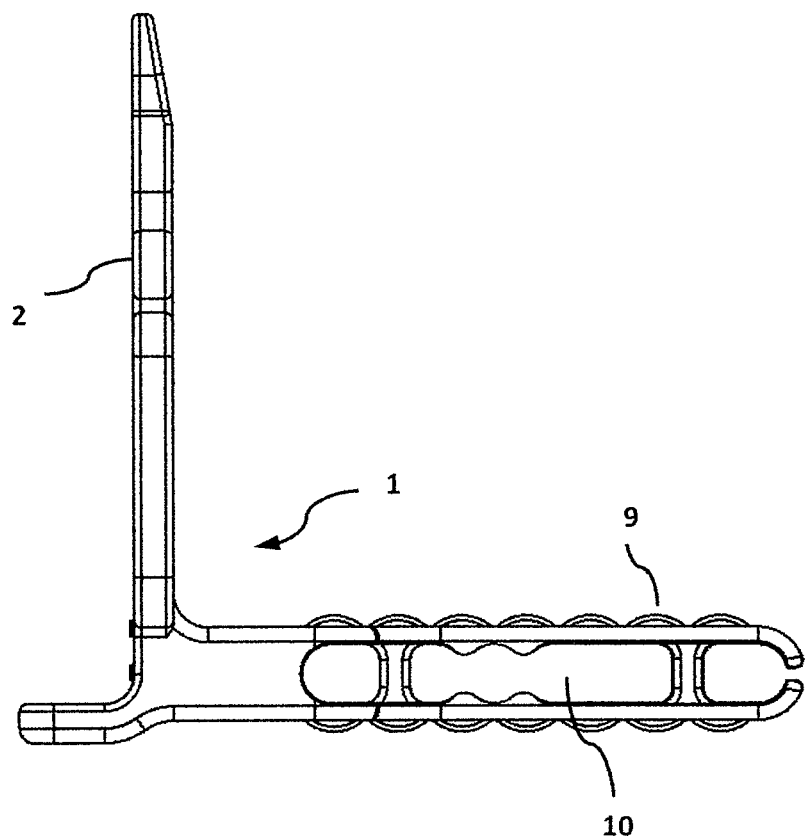
FIG. 3 is a side view of the sensor holder of FIG. 1.
Figure 4:
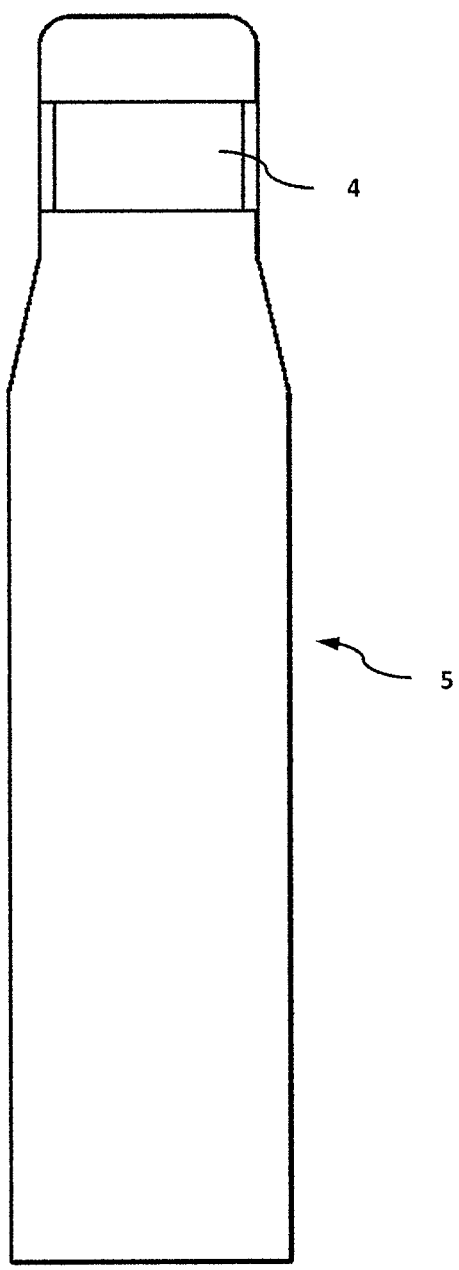
FIG. 4 illustrates a top view of a sensor sheath with a strap firmly sealed to the edges of the sheath.
Figure 5:
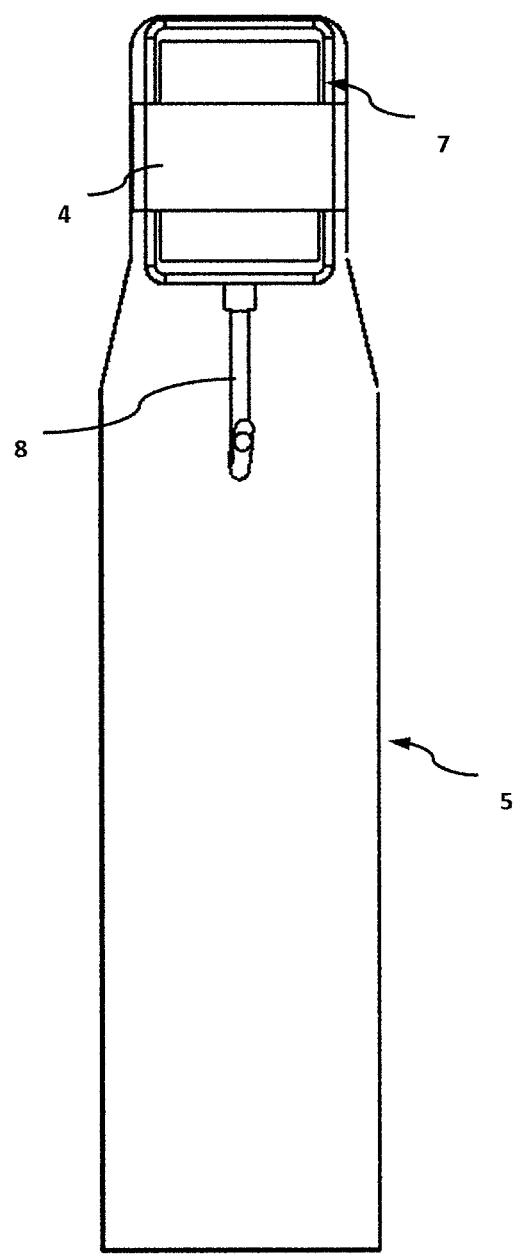
FIG. 5 shows a top view of a sensor sheath according to the present invention with a sensor inserted inside.
Figure 6:
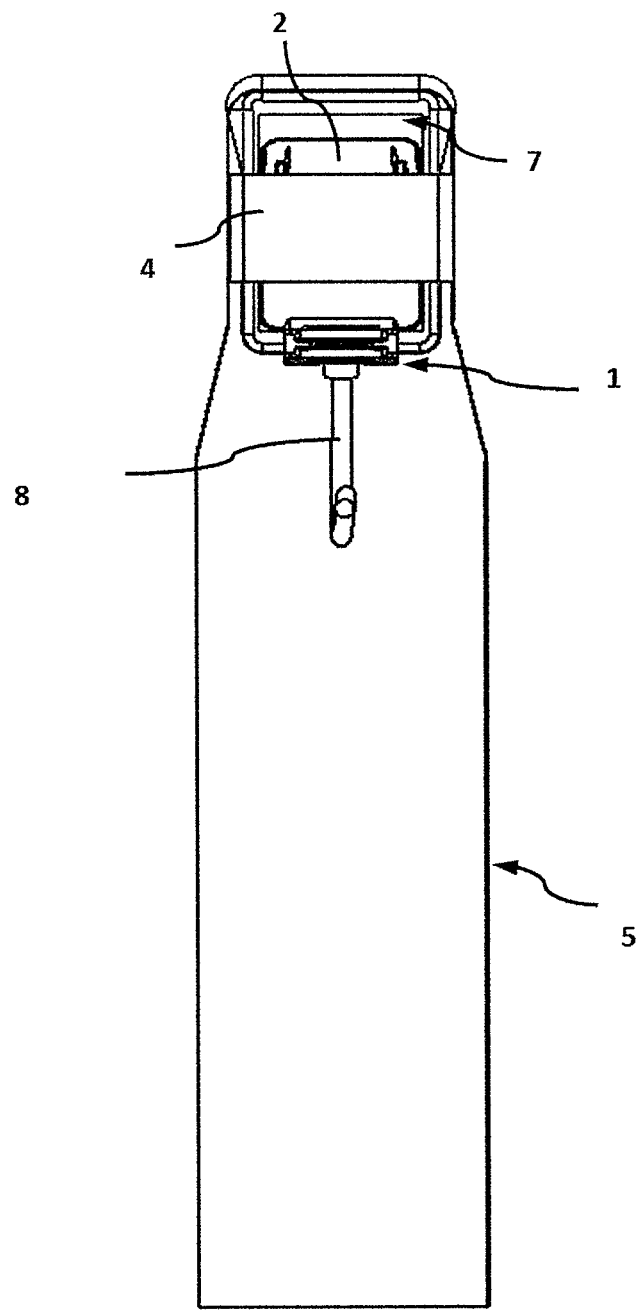
FIG. 6 shows a top view of the sensor/sensor sheath combination of FIG. 5 in use with the strap of the sheath being affixed to the sensor holder of the present invention.

In accordance with example aspects described herein, a sensor holder and sheath are provided for X-ray image acquisition. Focusing now descriptively on the drawings, in which similar reference characters denote similar elements throughout the several views, the figures illustrate a sensor holder with a backing plate, having one or more spring arms and affixed to or formed contiguously with a proximal end of a bite block of the holder, and a sensor sheath adapted to removably secure a sensor to the backing plate for X-ray acquisition.

Holder 1

Figure 8:
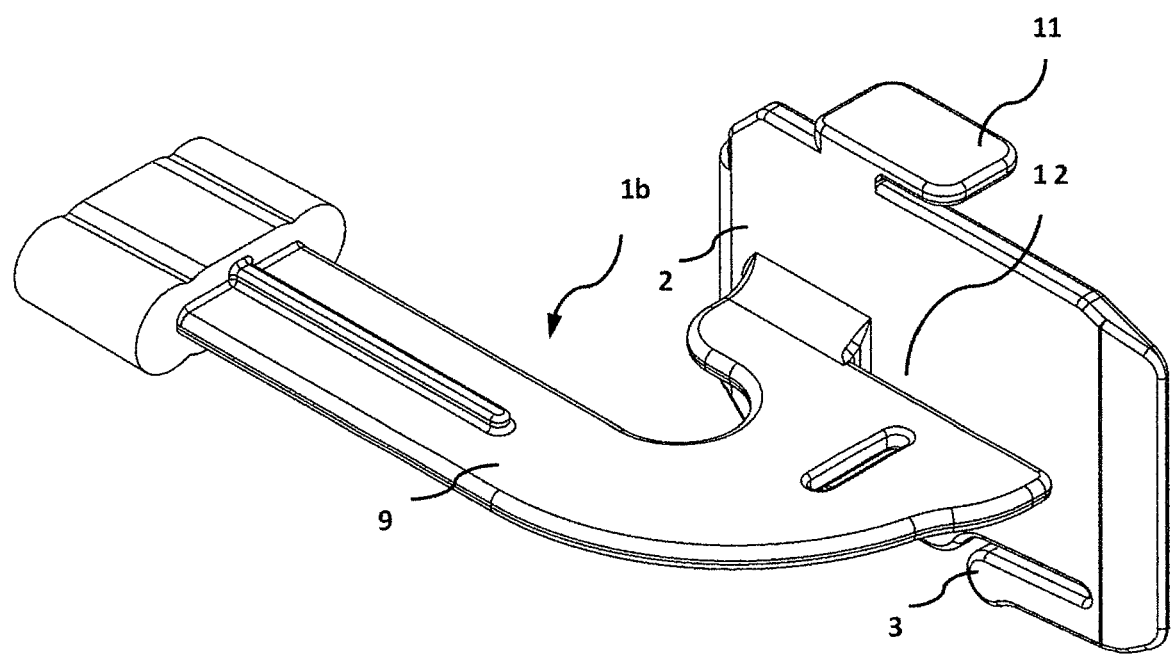
FIG. 8 shows a perspective view of an alternate embodiment of the holder, showing a holder for bitewing horizontal X-ray acquisitions.
Figure 10:
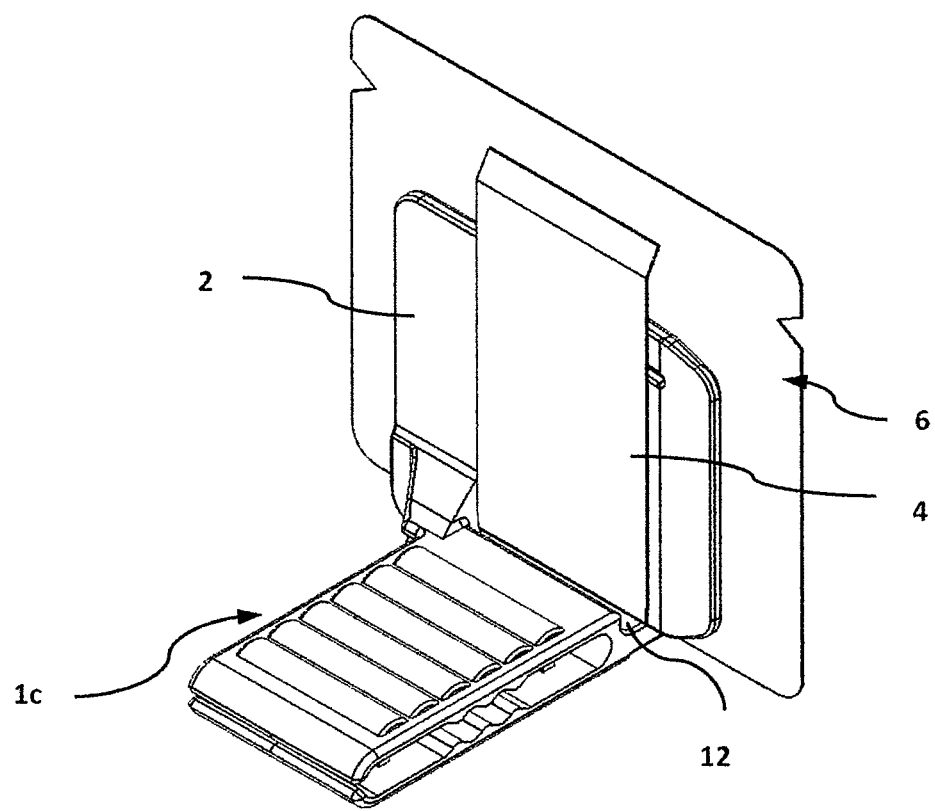
FIG. 10 is an upper perspective view of the holder of FIG. 1, connected to an alternate embodiment of the sensor sheath of the present invention, which alternate embodiment is a phosphor plate barrier with a strap sealed to it for engaging with the backing plate of the sensor holder.

Turning now to the sensor holder of FIG. 1, a backing plate 2 extends from the proximal end of a bite block 9. The backing plate 2 has a plurality of spring arms 3 which project outwardly from the backing plate 2. The backing plate is made of a fairly stiff material to ensure that an affixed sensor 7 is in parallel alignment with an aiming ring (not shown) for X-ray acquisition. The spring arms are adapted to slide easily under the strap 4 of a sensor sheath 5 and pull on the sheath 5 to tighten it which in turn keeps the sensor 7 in place. Alternative embodiments herein may also have sensor alignment tabs 11 to prevent the rotation of the sensor 7 when in use. This is especially helpful for posterior periapical and bitewing horizontal X-ray acquisitions wherein the sensor is attached to the backing plate in its horizontal position, (FIGS. 8 and 10).

The bite block 9 of the holder has slots 10 in which an aiming arm (not shown) is inserted preferably through a friction fit manner for further connection to an aiming ring (not shown). The bite block and holder in general may be of myriad shapes and sizes appropriate to allow for disparate positioning in the mouth of a patient during image acquisition procedures. As is known in the art, the bite block 9 of the X-ray sensor holder will be positioned in a patient's oral cavity (not shown) and the patient will be instructed to bite upon the block. This locates the secured X-ray sensor during the ensuing dental imaging acquisition procedure. Alternative embodiments of the holder may have a channel 12 (FIG. 8) in which a strap 4 of a sheath 5 fits. Another alternative embodiment may have an arrow 13 on a side of the backing plate to indicate the direction of insertion of the holder 1 under the strap 4.

Sheath 5

The sensor sheath 5 is adapted for connection to the backing plate 2 of a holder by the use of a strap 4 sealed to the sheath. The strap 4 can be affixed onto one side of the sheath by conventional methods used in the industry such as by heat staking or welding it along the short edges only. Alternatively, the strap 4 can be a loop around the sensor sheath 5 and preferably, it is made of a thick film strip capable of withstanding the force exerted by the spring arms 3 of the holder 1.

The X-ray sensor 7 slides easily into the sheath when the sheath is not engaged to the holder. When the holder 1 is then slid in under the strap 4 of the sheath 5, the spring arms 3 pull up on the strap 4 which in turn pulls up on the sheath 5 and tightens it around the sensor 7 to keep it 7 in place.

Different shapes and sizes of the sheath and strap, such as the phosphor plate barrier envelope/sheath 6 (shown in FIG. 10), can be realized for varied sensors and dental X-ray acquisition positions. The cable 8 of the X-ray sensor allows for transmission of the sensor data to a receiver in a conventional manner.

In accordance with this invention, the sheath 5 may be an X-ray sensor sheath that is adapted with a simple, flexible and mildly elastic plastic band that is firmly attached on the edges to a preferably clear film of sheath through such conventional methods as welding or heat staking. The strap 4 is attached at a position on the sheath such that the it pulls on the sheath 5 to tighten it around the sensor when the backing plate of a holder is inserted to fit tightly underneath it.

Alternative Embodiments of Invention

The holder is preferably molded from a single piece of thermoplastic such as polyethylene to ensure that X-rays pass evenly and unhindered therethrough.

Figure 7:
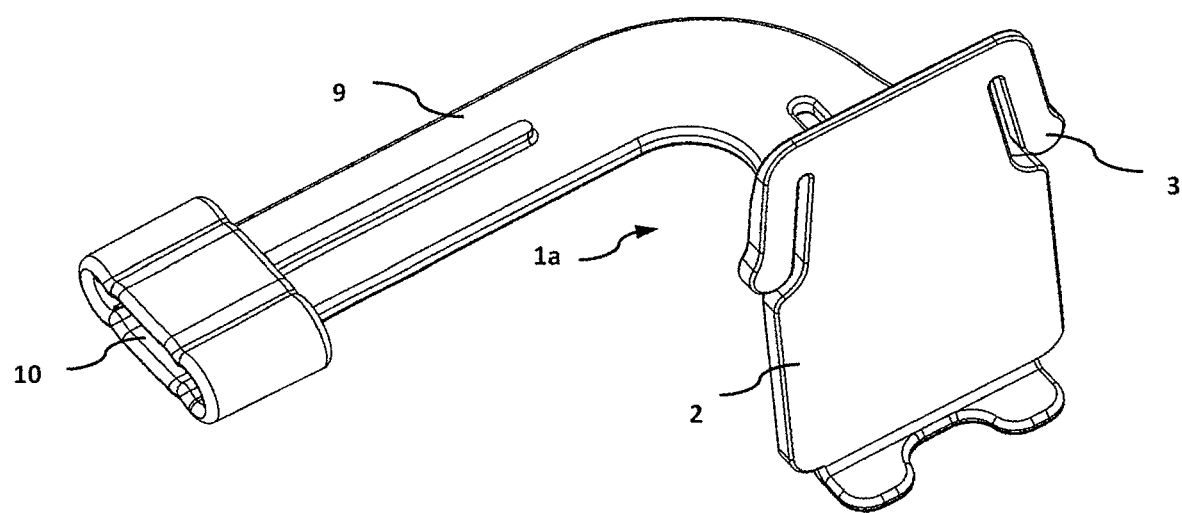
FIG. 7 illustrates a perspective view of an alternate embodiment of the holder, showing a holder for bitewing vertical X-ray acquisitions.
Figure 9:
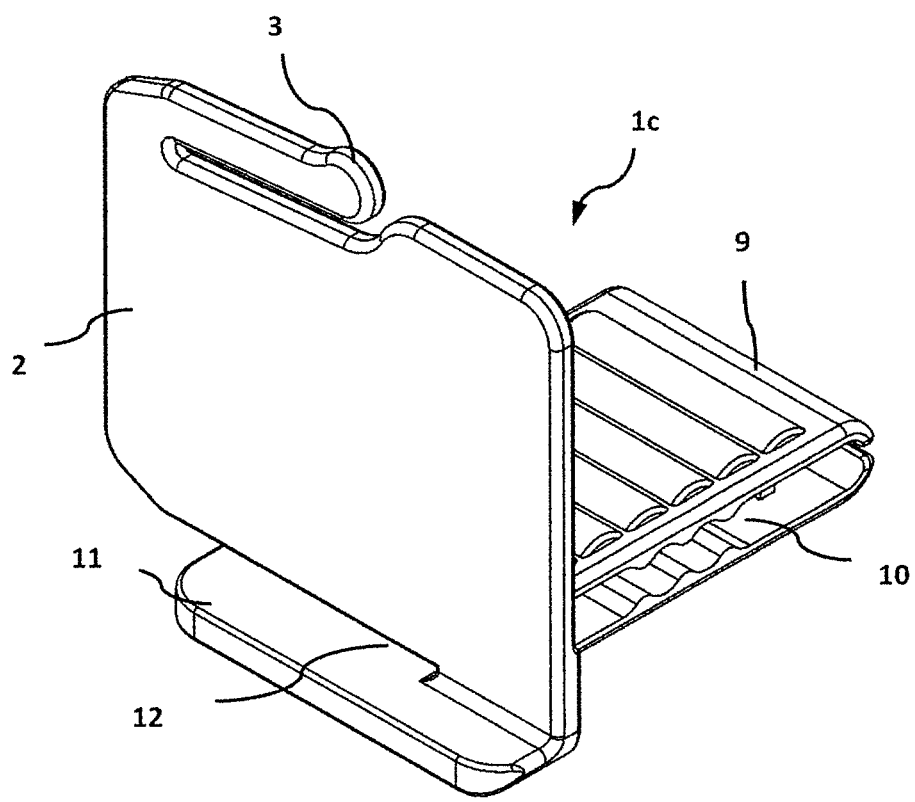
FIG. 9 illustrates a perspective view of an alternate embodiment, showing a posterior holder for X-ray acquisitions of the posterior teeth.
Figure 11:
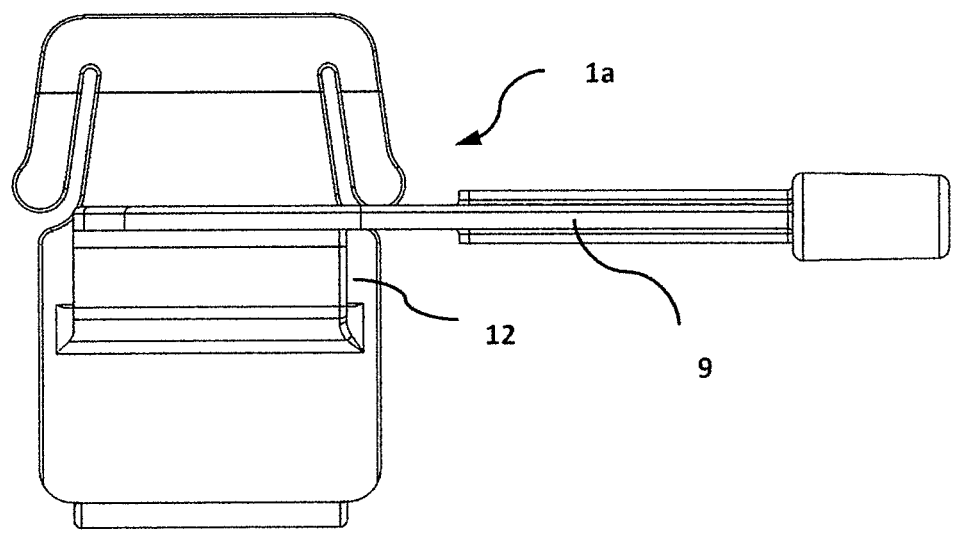
FIG. 11 shows a rear view of the holder of FIG. 7.
Figure 12:
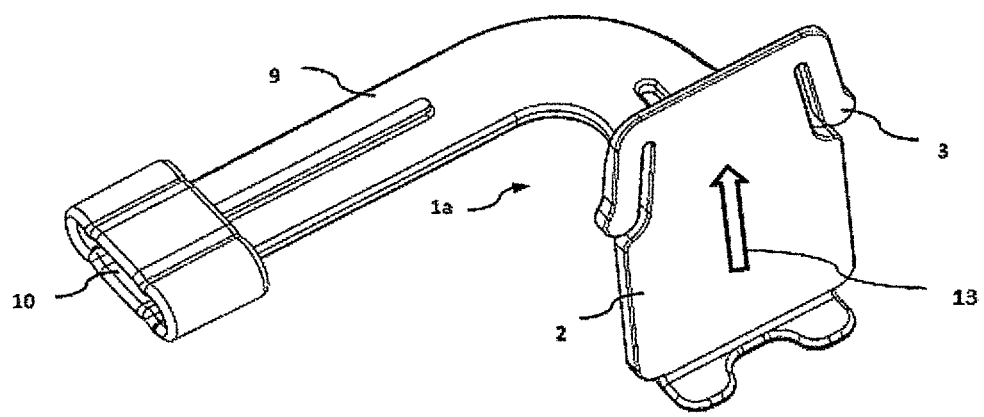
FIG. 12 shows an alternative embodiment of the holder with an arrow on a side of the backing plate.
Figure 13:
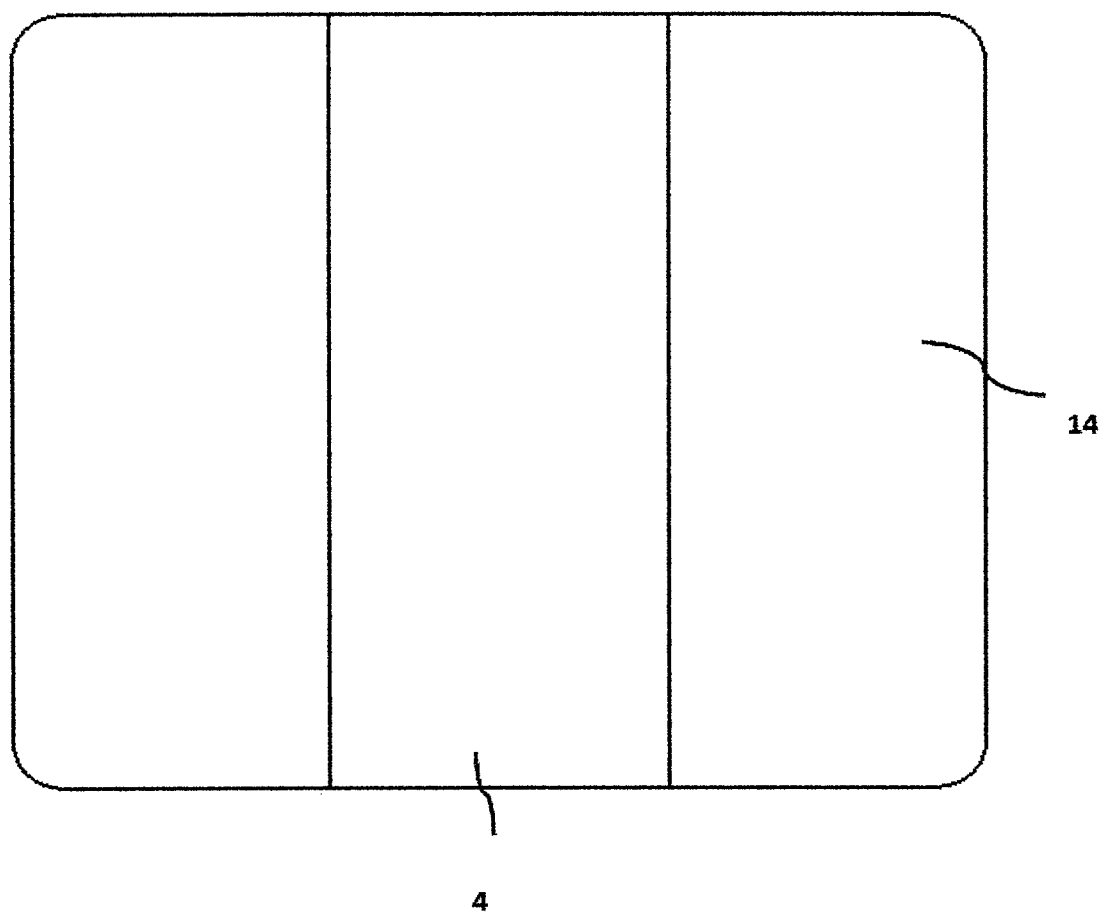
FIG. 13 illustrates the back film and strap of another embodiment of the phosphor plate barrier of the invention
Figure 14:
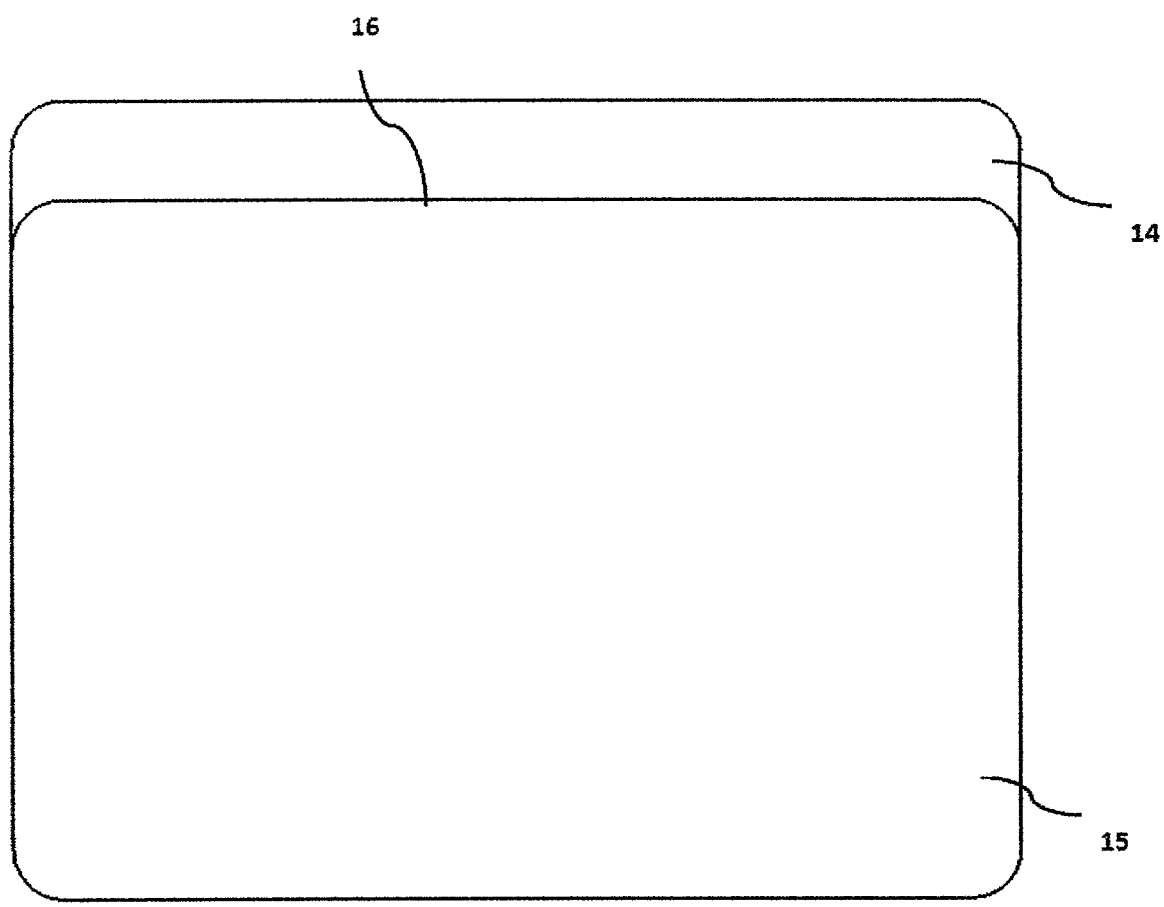
FIG. 14 illustrates the back film of FIG. 13 welded to the front film.
Figure 15:
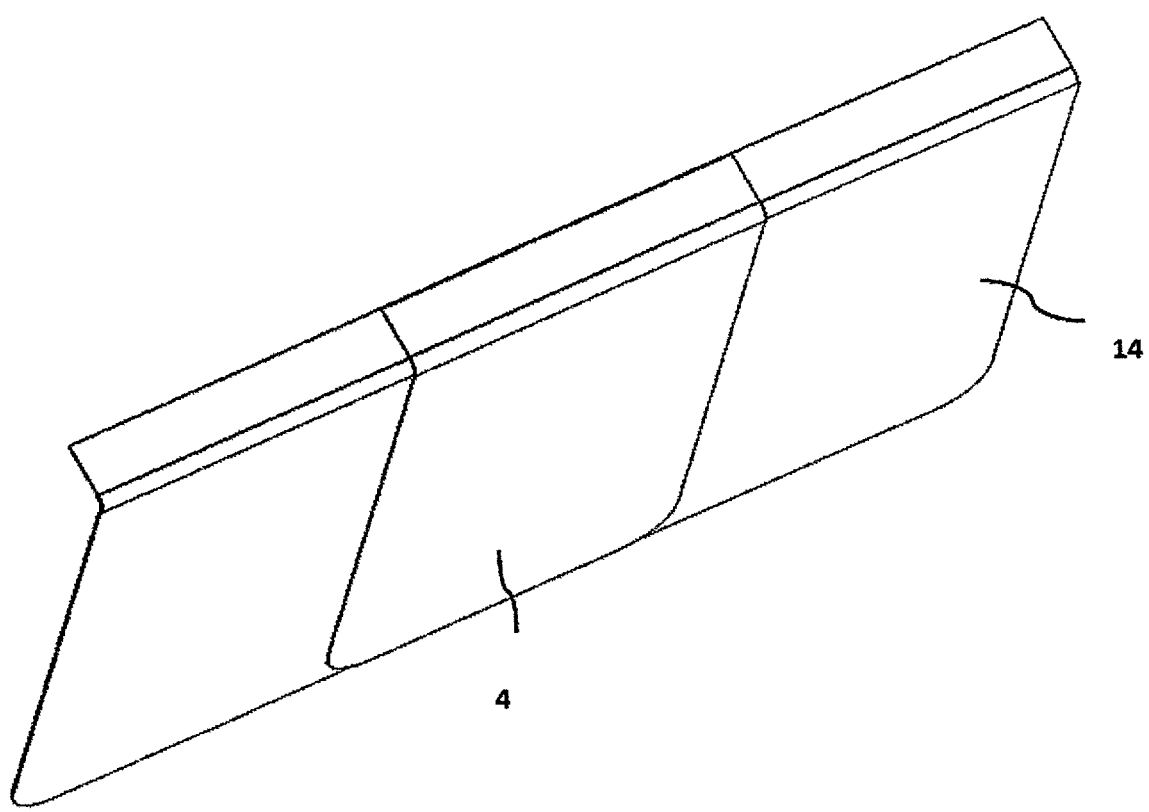
FIG. 15 shows an upper perspective view of the back film and strap of FIG. 13 with the upper part of the back film bended.
Figure 16:
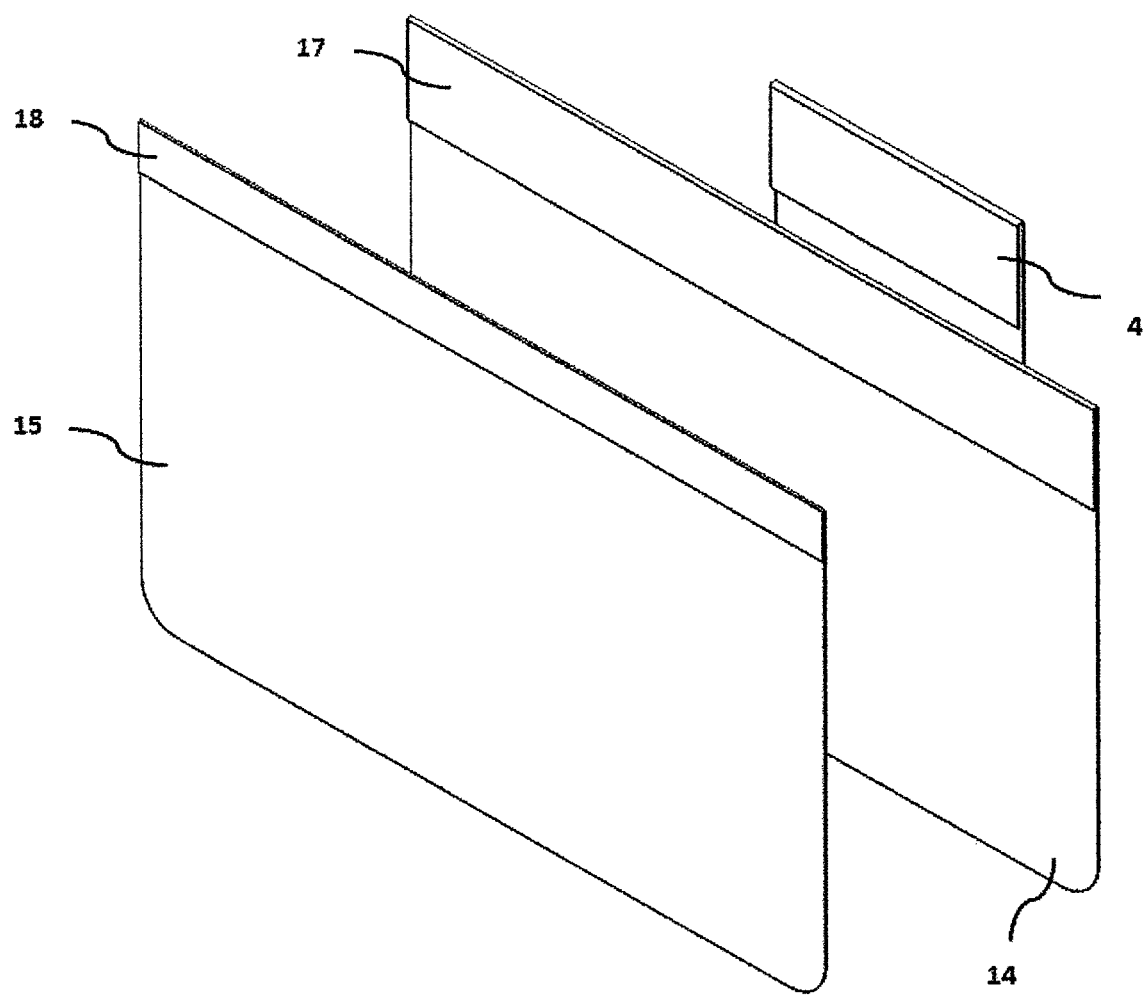
FIG. 16 is an exploded view of the phosphor plate barrier embodiment of FIG. 13 showing the back film, front film and strap.

FIGS. 7-9 show alternative embodiments of the sensor holder. FIG. 10 shows an alternative embodiment of the sheath in use Turning now to FIG. 7, an illustration of a bitewing vertical holder 1*a* is shown. A backing plate 2 having spring arms 3 projecting outwardly from said backing plate 2 is extends contiguously from the proximal end of an elongate bite block 9. The bite block 9 is joined to the backing plate 2 at a mid-region so it rests along the occlusal arch of the teeth to be radiographed. Located at a first end of the bite block 9 are slots for a conventional aiming arm (not shown) for connection to an aiming ring (not shown). Located at a second end of the bite block 9 is a channel 12 (shown in FIG. 11) for receiving the strap 4 of a sheath 5 of the present invention.

FIG. 8 illustrates a bitewing horizontal holder 1*b* with a backing plate 2 and an elongate bite block 9. In addition, a sensor alignment tab 11 may extend from the backing plate to correctly position an attached sensor during X-ray acquisitions to minimize distortion and improper focus resulting from incorrect alignment. A channel 12 is provided for receiving the strap 4 of a sensor sheath 5 of the present invention.

FIG. 9 shows a posterior holder 1*c* for imaging teeth in the posterior region of an oral cavity comprising a backing plate 2, spring arm 3 and bite block 9. Like other embodiments, the holder is provided with a channel 12 for receiving the strap 4 of a sheath 5 of the present invention. A sensor alignment tab 11 allows for arranging a sensor in an appropriate position for imaging.

FIG. 10 shows an alternative embodiment of a sheath in use. A strap is preferably permanently attached to a phosphor plate barrier/sheath 6 using conventional means. The strap is likewise preferably a simple, flexible and mildly elastic plastic band that is firmly welded or heat staked to the phosphor plate barrier. In another alternative embodiment of the phosphor plate barrier, as shown in FIGS. 13-16, the barrier has a front film 15 and a back film 14 wherein the front film 15 is welded or attached in similar fashion along the sides and bottom edges to the back film 14 and between which a phosphor plate (not shown) is inserted. The top edge 16 of the front film 15 is not welded to the back film 14 providing an entrance for insertion of the phosphor plate. The back film 14 is has a strap 4 welded to it along the short edges of the strap 4. When the phosphor plate is inserted, the back film 14 is bended 17 and sealed to the front film 15 after a protective liner 18 on the front film 15 is removed to expose an adhesive coating (not shown). This makes the strap 4 of the barrier tight and ready for insertion of a holder 1.

It will be appreciated by skilled persons in the art that the elements of the abovementioned embodiments can be extended to other conventional holders such as but not limited to endodontic holders and that many variations of the embodiments are possible without departing from the spirit and scope of the invention.

Operation of Preferred Embodiment

The operation of a preferred embodiment, shown in FIG. 1 involves easily sliding a sensor 7 into a sheath of the present invention. The backing plate 2 of the holder 1 is then slid in underneath the strap 4 of the sheath 5. The spring arms 3 of the backing plate then pull up on the strap 4 which tighten the sheath 5 to keep the sensor in place. The slot 10 of the bite block 9 is affixed with an aiming arm (not shown) which in turn is affixed with an aiming ring (not shown). The bite block is hereafter positioned in the oral cavity by clenching the buccal surfaces of the maxilliary and mandibular teeth on the block so that the sensor is appropriately positioned, for example, perpendicularly to the interproximal region of the tooth or teeth to be examined. The dental professional can then align the aiming ring and the X-ray unit for image acquisition.

What has been described and illustrated herein is a preferred embodiment of the invention along with some of its variations. The terms, descriptions and figures used herein are set forth by way of illustration only and are not meant as limitations. Those skilled in the art will recognize that many variations are possible within the spirit and scope of the invention in which all terms are meant in their broadest, reasonable sense unless otherwise indicated. Any headings utilized within the description are for convenience only and have no legal or limiting effect.

INDEX OF ELEMENTS

1: Anterior Holder
1*a*: Bitewing Vertical Holder
1*b*: Bitewing Horizontal Holder
1*c*: Posterior Holder
2: Backing Plate
3: Spring Arm
4: Strap
5: Sheath
6: Phosphor Plate Barrier Envelope
7: Sensor
8: Sensor Cable
9: Bite Block
10: Slot/Aperture
11: Sensor Alignment Tab
12: Channel
13: Arrow
14: Back Film
15: Front Film
16: Top Edge
17: Bend
18: Protective Liner

The invention claimed is:

1. A dental X-ray imaging media holder and sheath comprising:
a dental X-ray imaging media holder with a bite block, said bite block having a proximal end and a distal end;

a backing plate extending from the proximal end of the bite block; and a sheath comprising a protective cover and a strap attached thereto;

wherein the strap is configured to removably affix the sheath and a sensor within the sheath to the backing plate of said holder, and wherein one or more spring arms of the backing plate are configured to slide under the strap of said sheath to pull on the sheath to tighten the sheath around the sensor.

2. A method of operating a dental X-ray imaging media holder for X-ray acquisitions of one or more teeth, comprising:

providing a sensor with a sheath, said sheath having a strap for removably engaging with one or more spring arms of the holder, sliding one or more spring arms of a backing plate of the holder under the strap to secure the sensor and sheath onto the holder, affixing an aiming arm to slots of a bite block of the sensor holder to align an aiming ring of the aiming arm with the sensor, placing a bite block of the holder in the oral cavity such that the teeth to be imaged are between the sensor and the aiming ring, and acquiring an X-ray image of the teeth.

* * * * *